United States Patent [19]
Fabro et al.

[11] Patent Number: 5,934,276
[45] Date of Patent: Aug. 10, 1999

[54] ORAL TUBE HOLDER

[75] Inventors: Robert S. Fabro, Rancho Cucamonga; Angel Pelayo, Glendale, both of Calif.

[73] Assignee: Pelabro, Inc., Rancho Cucamonga, Calif.

[21] Appl. No.: 08/954,274

[22] Filed: Oct. 20, 1997

[51] Int. Cl.⁶ .................................................. A61M 16/00
[52] U.S. Cl. ................................ 128/207.17; 128/207.14
[58] Field of Search .......................... 128/207.17, 207.14, 128/207.26; 604/79, 174, 179; 24/164, 172, 318, 625, 543

[56] References Cited

U.S. PATENT DOCUMENTS

| | | |
|---|---|---|
| 2,820,457 | 1/1958 | Phillips . |
| 2,908,269 | 10/1959 | Cheng . |
| 3,946,742 | 3/1976 | Eross . |
| 4,223,671 | 9/1980 | Muto . |
| 4,249,529 | 2/1981 | Nestor et al. . |
| 4,392,857 | 7/1983 | Beran . |
| 4,516,293 | 5/1985 | Beran . |
| 4,592,351 | 6/1986 | Smith et al. . |
| 4,744,358 | 5/1988 | McGinnis . |
| 5,009,227 | 4/1991 | Nieuwstad .......................... 128/207.17 |
| 5,345,931 | 9/1994 | Battaglia . |
| 5,419,319 | 5/1995 | Werner .............................. 128/207.17 |
| 5,490,504 | 2/1996 | Vrona . |
| 5,555,881 | 9/1996 | Rogers et al. . |

*Primary Examiner*—John G. Weiss
*Assistant Examiner*—Charles W. Anderson
*Attorney, Agent, or Firm*—Joseph E. Mueth

[57] ABSTRACT

An endotracheal oral tube holder made up of two separate parts, the face anchor and the tube cradle. The face anchor has buckles which hold a head harness. The face anchor is made of a material which allows it to conform to the contours of the face of the patient. The face anchor also has a pivot hole to which the tube cradle is affixed by a rivot. The endotrachael tube moves transversely across the mouth due to the pivoting action of the tube cradle. The tube cradle has a "living hinge" which allows the endotracheal tube to move longitudinally.

16 Claims, 4 Drawing Sheets

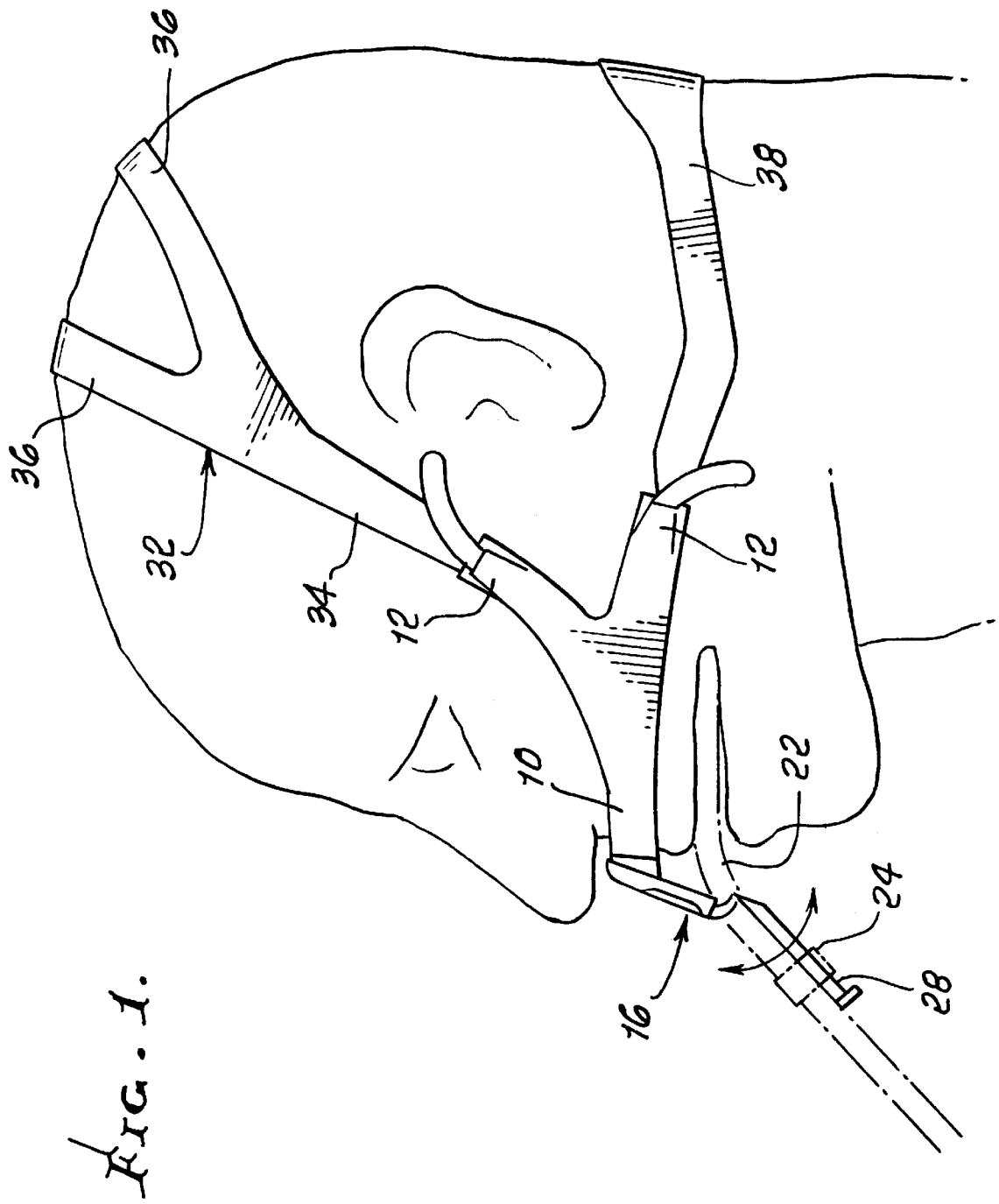

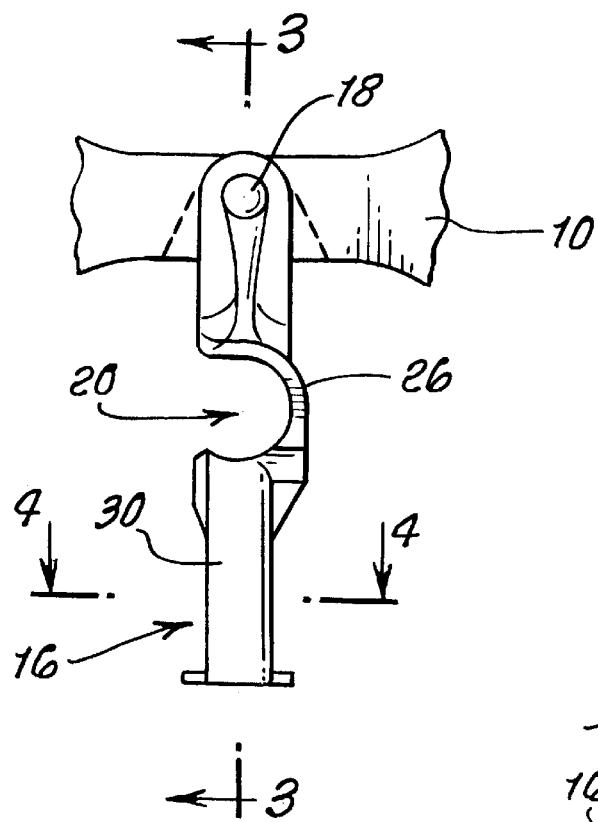
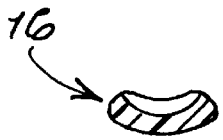
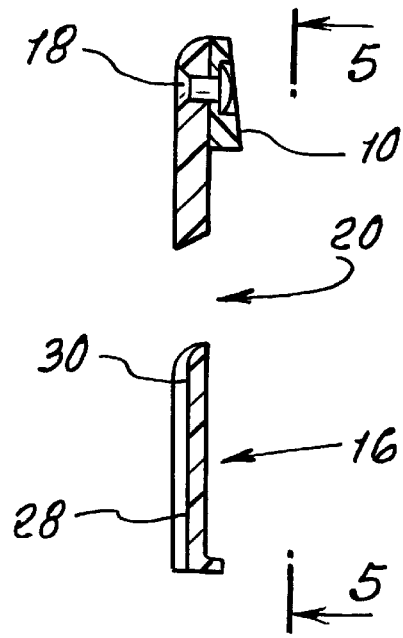
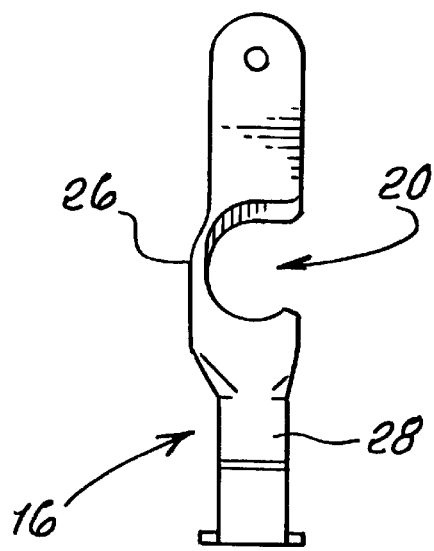

ORAL TUBE HOLDER

FIELD OF INVENTION

This invention relates to medical devices and more particularly, to an improved holder for oral tubes. For example, endotracheal tubes.

BACKGROUND OF THE INVENTION

During oral intubation, an endotracheal tube is inserted into the patient's trachea. Typically the endotracheal tube is secured to the patient's face by using adhesive tape. The use of tape results in a variety of problems. A problem with adhesive tape is that it must be reapplied in a timely manner. The constant removal and reapplying causes the skin on the face to break down creating sores and leaving the patient susceptible to infection. Tape also does not allow the movement of the endotracheal tube from one spot of the mouth to another to prevent pressure sores caused by the endotracheal tube. The tape also obstructs access to the mouth for routine or emergency care. Furthermore, the patient's secretions cause the tape to lose its adhesive properties and this can cause the endotracheal tube to come out of the patient's trachea.

Previous devices have attempted to solve these problems associated with the use of adhesive tape. However, problems continue to exist and new problems are created in connection with these devices. For example, in Phillips U.S. Pat. No. 2,820,457 (Jan. 21, 1958) and Cheng U.S. Pat. No. 2,908,269 (Oct. 13, 1959), these devices cover the mouth making oral care difficult. Furthermore, during an oral intubation, the endotracheal tube first must be threaded through these devices and then through the patient's trachea. This awkward procedure makes it difficult for the practitioner when inserting the endotracheal tube to visualize the patient's trachea, thus making this device potentially dangerous.

McGinnis, U.S. Pat. No. 4,744,358 (May 17, 1988) relates to an endotracheal tube holder including a rigid endotracheal tube platform having a clamp for clamping an endotracheal tube into a tube channel. The tube platform is supported with respect to the patient's head by a rigid face plate frame secured to the face of a patient by a head harness. The rigid frame rides on the patient's chin. Battaglia U.S. Pat. No. 5,345,931 (Sep. 13, 1994), describes a complicated endotracheal tube holder having many parts including a rigid face plate which is also adapted to ride on the patient's chin. Werner, U.S. Pat. No. 5,419,319 (May 30, 1995) discloses a variable position endotracheal tube holder which includes a face piece having a stiff arcuate transverse portion adapted to pass between the nose and upper lip of the patient, and a pair of downwardly extending wings at either end of the transverse portion. The lateral portion of the face piece has upper and lower flanges which define a groove which receives and retains a movable support for holding the endotracheal tube. These rigid or stiff face plates are not conducive to patient comfort. These devices cover the mouth too much and make it difficult to suction or otherwise provide oral access.

Rogers et al, U.S. Pat. No. 5,555,881 (Sep. 17, 1996) relates to an endotracheal tube holder which has a collar formed from two body portions clamped together to form an adjustable clamping orifice designed to accommodate and grip endotracheal tubes of varying diameters. A padded lip bumper is attached to the endotracheal tube holder.

Smith et al, U.S. Pat. No. 4,592,351 (Jun. 3, 1986) discloses a holder for endotracheal or nasotracheal tubes that comprises a plastic face guard, a plastic tube-grasping section, and a flexible connecting section comprising a unitary sheet of plastic which, once formed, is rendered stiff by the channel constituting the connecting section. The face guard can ride above or below the mouth. The device of Smith does not permit any transverse or longitudinal movement of the tracheal tube when in place in the trachea.

Vrona et al, U.S. Pat. No. 5,490,504 (Feb. 13, 1996) describes an endotracheal tube attachment device for securing an endotracheal tube to a patient and allowing lateral positioning and locking of the tube without removing the tube from the patient. The device comprises an elongated strip made from flexible material which is attached to an upper lip of a patient by an adhesive pad. The tube holder is slideably mounted on a T-shaped track or rail forming part of the strip. The T-shape produces rigidity. The tube holder portion does not provide for any longitudinal movement of the tube once it is in place.

Eross U.S. Pat. No. 3,946,742 (Mar. 30, 1976), discloses a device which, while having some superficial resemblance to the present invention, is vastly different. The Eross device is intended to be strapped on the chin, whereas the present invention is intended to be strapped on the upper lip. The face anchor in the Eross device is a thick plastic. In the present invention, the face anchor is a thin plastic intended to conform to the contours of the patient's face. This difference in the face anchor allows the device of the present invention to be more comfortable. The Eross device has a semi-rigid bite block to protect the endotracheal tube. In the present invention, a bite block is not used, resulting in added comfort to the patient. Both the Eross and the present device swivel on a pivot to move the endotracheal tube from side to side in the mouth, but the device of the present invention also allows the endotracheal tube to move up and down. The Eross device has a neck strap to hold his device, whereas the present invention has two straps to hold a conformable face anchor, which provides far more security without sacrificing comfort. In the present invention, the face anchor rides on the front of the patient's face between the bottom of the nose and the upper lip. In Eross, the entire endotracheal tube holder, riding on the chin, is subject to undesirable movement due to the patient's inadvertent raising and lowering of the mandible. The Eross device does not provide an upward pull to keep the device on the lip and, in fact, the Eross device would tend to slip down and off the lip.

In Muto U.S. Pat. No. 4,223,671 (Sep. 23, 1980), Beran U.S. Pat. No. 4,392,857 (Jul. 12, 1983) and Beran U.S. Pat. No. 4,516,293 (May 14, 1985) these devices cover the mouth, preventing oral care. The devices do not allow the endotracheal tube to be moved for side to side and thus tend to produce pressure sores in the mouth. In addition, Beran's device uses adhesive to secure itself to the patient's face which creates a breakdown on the skin and makes itself susceptible to slippage due to secretions from the patient.

Nestor et al, U.S. Pat. No. 4,249,529 (Feb. 10, 1981) discloses an endotracheal tube holder having a body which is secured by a pair of head encircling straps to overlie the patient's mouth and portions of the cheeks. The straps have one-way tightening adjustability by pawl action.

Nieuwstad, U.S. Pat. No. 5,009,227 (Apr. 23, 1991) relates to an endotracheal tube holder that is provided to hold both an endotracheal tube and a feeding tube in a side by side relationship. Two separate passageways are provided to hold each tube. A surrounding collet provides compression force to hold the endotracheal tube in position relative to the holder.

SUMMARY OF THE INVENTION

A novel oral tube holder adapted to be received on the face and over the head of the patient to retain the tube in place through the mouth of the patient which comprises:

(1) a face anchor which is manually conformable to the contours of the patients face;

(2) pivotally connected to said face anchor for extending below the patient's mouth, a tube cradle which allows transverse pivotal movement of said tube cradle with respect to said anchor, said tube cradle including means for restraining and holding a tube in the patient's mouth; and (3) strap means for holding said face anchor against the patient's face and holding said face anchor and tube cradle in place.

A flat face anchor in the form of a thin sheet of manually manipulatable, flexible, conformable plastic, in the shape of two "Y" shaped portions integrally joined by a common central portion, each of the Y shaped portions having spaced apart arms carrying buckles in proximity to their terminal ends.

In accordance with this invention, the highly improved oral tube holder is comprised of two separate parts, with each part having two sectional parts.

The face anchor is made of a semi-rigid plastic material which is ergonomically configured so that it fits any face comfortably. The face anchor is molded as a flat member. By simple manual manipulation, the face plate can be conformed to the shape and size of the patient's face in the area beneath the nose and around the sides of the head. The face plate once shaped, retains its shape unless further manipulated, but has sufficient "give" to relieve pressure to the patient's face. The width of the face anchor is adapted specifically to dissipate the pressure that occurs when it is secured to the patient's face, thus preventing pressure sores. The thinness of the face anchor does not to occlude or obstruct the nose. The self-locking buckles operate to make it easy and quick to secure the device to the face.

The tube cradle which is also made of a semi-rigid plastic material, is configured to provide strength and stability to hold a variety of sizes of oral tubes. The cradle was designed with a 120° angle and a "living hinge" which provides three functions. First, it supports and guides any oral tube as it passes through the mouth and keeps the secretions of the patient from reaching where the endotracheal tube is secured to the device. Second, it provides the strength and stability to secure the oral tube even if other equipment is attached to the oral tube such as a ventilator circuit, capnograph monitor, etc. Finally, the cradle is adapted to be adjustable. The cradle adjusts so that the oral tube can more transversely across the mouth and longitudinally to avoid pressure sores.

The head harness comprises two straps made of an elastic plastic or rubbery material which are adapted to hug the head of the patient and hold the face anchor in place with little pressure on the face. The straps go through the self-locking buckles so that the device has an endless amount of adjustable points. The straps were also designed to have an upward pull so as to keep the device from slipping into the patients mouth.

DESCRIPTION OF PREFERRED EMBODIMENTS

Turning to the drawings:

FIG. 1 is a side view showing the overall oral tube holder of this invention in position around the head and on the face of the patient, with an endotracheal tube taped in place.

FIG. 2 is a partial frontal view of the oral tube holder of FIG. 1, showing the complete tube cradle without the endotracheal tube.

FIG. 3 is a sectional view along the line 3—3 in FIG. 2.

FIG. 4 is a sectional view along the line 4—4 in FIG. 2.

FIG. 5 shows the rear view of the tube cradle of FIG. 2.

Figure 6:
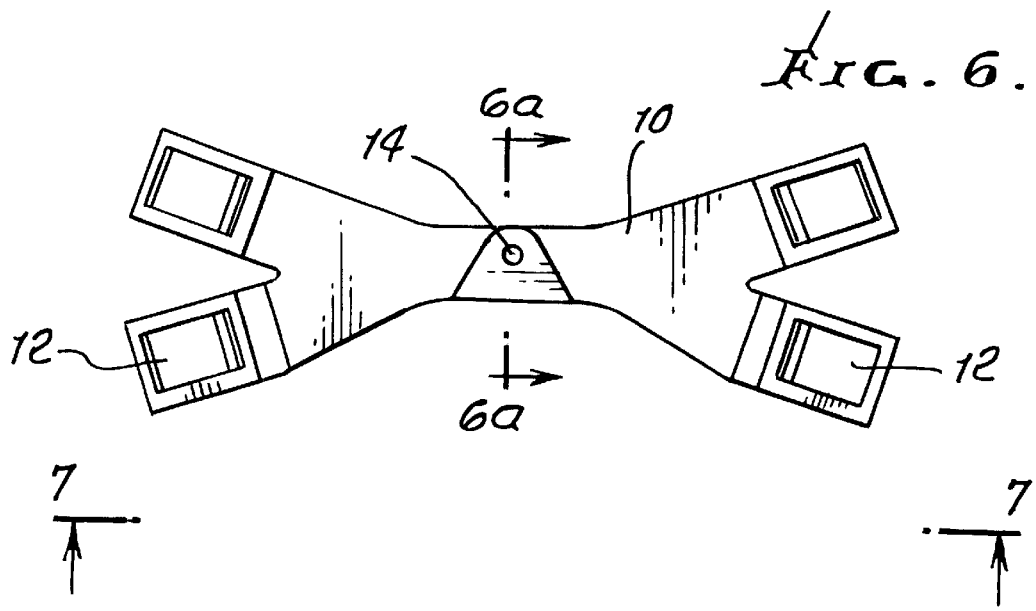
FIG. 6 shows the top view of the face anchor portion of the device in FIG. 1 in a planar condition prior to being conformed to the face contours of the patient.
Figure 7:
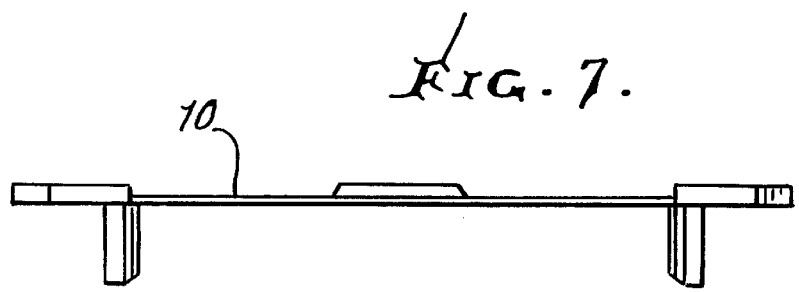
FIG. 7 is a side view taken from the perspective of line 7—7 in FIG. 6.
Figure 8:
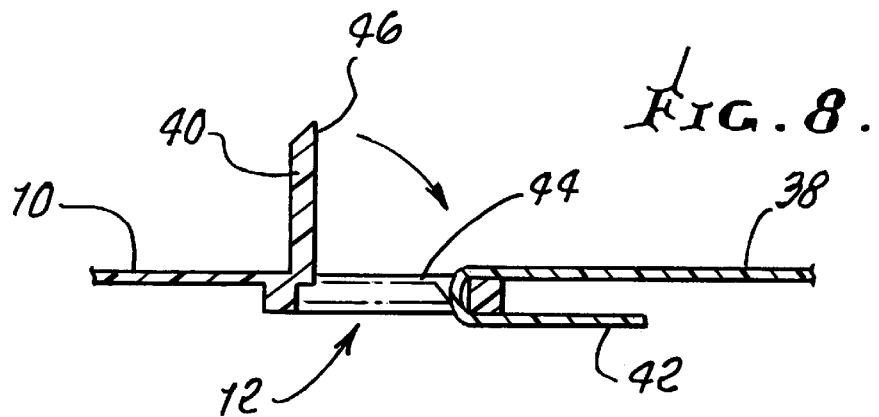
FIG. 8 shows one of the four self-locking buckles provided at each of the extremities of the face anchor, best seen in FIG. 6, with the buckle being in the open or non-engaged position.

Turning to the drawings in more detail, the face anchor 10 is made of polypropylene or other conformable plastic which when generally contoured to the shape of the patient's face, retains that shape while having the ability to yield slightly to relieve any pressure to the face. At its extremities, the face anchor 10 has four self-locking buckles 12 which are adapted to engage with the head harness as more fully described hereinbelow. The face anchor has a pivot hole 14 to which is pivotally held the tube cradle 16 by rivot 18. The tube cradle 16 has a generally "C"-shaped portion 20 into which an endotracheal tube 22 can be slidably inserted. The open side of the "C" is slightly unsize the external diameter of the endotracheal tube so that some force is required to insert the endotracheal tube into the tube cradle. Once the endotracheal tube 22 has been inserted, it cannot be easily dislodged without manual manipulative force. The tube cradle 16 can be made of the same material as the face anchor although other materials can be used since it may not be conformable and shape-retaining.

Figure 6A:
FIG. 6a is a sectional view taken along the line 6a—6a in FIG. 6.
Figure 9:
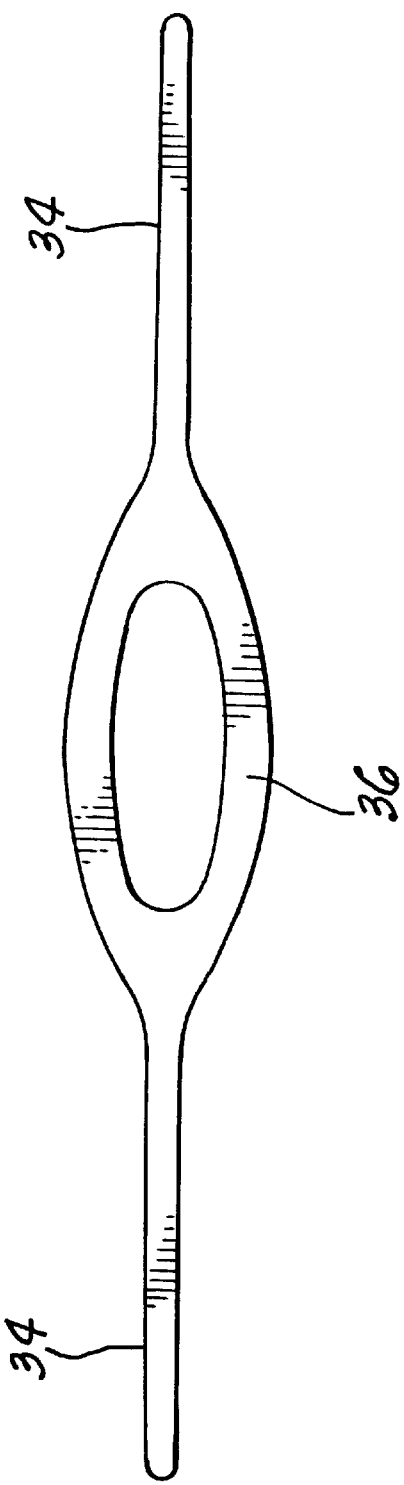
FIG. 9 is a plan view of the head harness portion which holds the crown of the patient's head.
Figure 10:
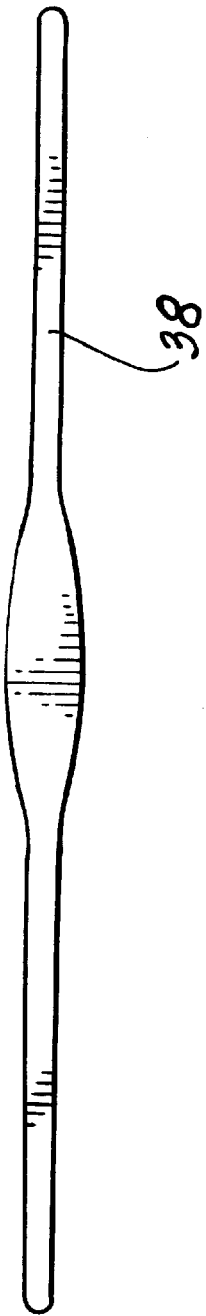
FIG. 10 is a plan view of the head harness portion forming the neck strap.

Normally, the endotracheal tube 22 is held by tape 24 to the tube cradle 16, as shown in FIG. 1. The rivot 18 holding the tube cradle 16 to the face anchor 16 is loose enough to permit transverse pivoting action of the tube cradle, together with the attached endotracheal tube, across the mouth of the patient. This direction of permissible movement is indicated by the curved arrow in FIG. 2. As shown in FIGS. 3 and 6a, the face anchor 10, at its center, is thicker at its lower margin to hold the face anchor 16 at an outwardly sloping angle, away form the patient's lips, see FIG. 1. The tube cradle 16 at the "C"-shaped portion 20 is of a thin cross-section 26 to provide a "living hinge" which securely supports the endotracheal tube and allows that portion 28 of the tube cradle 16 below the portion 20, as well as the endotracheal tube 22 which is taped thereto, to move longitudinally, that is, up and down, as is indicated by the small arrow in FIG. 1, without disturbing or exerting force on face anchor 10 or significantly effecting the position of the endotracheal tube within the trachea itself.

Portion 28, as best shown in FIG. 4, has a concave outer surface 30 for partially snugly receiving the endotracheal tube 22.

The head harness comprises two straps, the crown portion 32 holds the crown to the patient's head and is single strap 34 which splits into two straps 36. The other piece of the head harness is the neck strap 38. Each of these straps engage the face anchor at or around the outer lateral edges or margins.

The head harness is attached to the face anchor 10 by the self-locking buckles 12 which are easy and quick to secure. The buckles 12 are usually molded from a polyolefin plastic. Each of the buckles 12 has an integral hinged flap 40 which engages the free end 42 of the crown portion 32 or neck strap 38. The flap 40 is formed with the flap in the "down" position with respect to the rest of the buckle.

In use the flap 40 is pushed up through the opening 44. The memory of plastic causes the flap to have a tendency to be biased downwardly into the opening 48. Consequently, when the flap is pushed up, the free end 44 passed through the opening 44, and the flap is released, the flap will clamp down on free end 42. The beveled end 46 of the flap 40 also engages the surface of end 42 and further prevents slippage. The nurse or technician can easily disengage the flap 40 by digitally pushing up on the flap to remove or adjust the head harness.

Having fully described the invention, the invention is defined by the following claims.

We claim:

1. A novel oral tube holder adapted to be received on the face and over the head of the patient to retain the tube in place through the mouth of the patient which comprises:

(1) a face anchor which is manually conformable to the contours of the patients face;

(2) pivotally connected to said face anchor for extending below the patient's mouth, a tube cradle which allows transverse pivotal movement of said tube cradle with respect to said anchor, said tube cradle including means for restraining and holding a tube in the patient's mouth; and (3) strap means for holding said face anchor against the patient's face and holding said face anchor and tube cradle in place.

2. The oral tube holder of claim 1 wherein the face anchor and tube cradle are pivotally connected at a point adapted to ride below the patient's nose and above the upper lip.

3. The oral tube holder of claim 1 wherein said tube cradle has a living hinge to allow the lower free end of said tube to move longitudinally toward and away from the patient's chin.

4. The oral tube holder of claim 7 wherein said side margins are provided with buckles.

5. The oral tube holder of claim 4 wherein said buckles include an integrally formed hinged flap, a close fitting opening for receiving said flap, said flap being biased to move toward said opening to clamp on said strap when the end of the strap is passed through said opening.

6. The oral tube holder of claim 1 wherein the center of the face anchor is thicker at its lower margin to hold said tube cradle away from the patient's lips.

7. The oral tube holder of claim 1 wherein said strap means comprises a crown strap for passing over the patient's head and a neck strap for passing around the back of the neck, said straps engaging the side margins of said face anchor and adapted to hold it firmly in place against the face above the mouth.

8. The oral tube holder of claim 7 wherein said straps are an elastomeric material.

9. The oral tube holder of claim 1 wherein the tube holder includes a C-shaped lateral opening for snugly receiving and holding the tube following lateral insertion.

10. The oral tube holder of claim 1 wherein the face anchor is made of a manually manipulatable, conformable, shape-retaining plastic.

11. The oral tube holder of claim 1 wherein said tube holder is pivotally connected to said face anchor by a rivot.

12. A flat face anchor in the form of a thin sheet in the shape of two "Y" shaped portions integrally joined by a common central portion, each of the Y shaped portions having spaced apart arms carrying buckles in proximity to their terminal ends.

13. The flat face anchor of claim 12 wherein said central portion has a rivot hole therethrough.

14. The flat face anchor of claim 12 wherein said thin sheet is made of a manually manipulatable, conformable, shape-retaining plastic.

15. The flat face anchor of claim 12 wherein said buckles are adapted to receive a strap and include an integrally formed hinged flap, a close fitting opening for receiving said flap, said flap being biased to move toward said opening to clamp on said strap when the end of the strap is passed through said opening.

16. The flat face anchor of claim 12 wherein the center of said face anchor is thicker in cross section at its lower margin.

* * * * *